United States Patent [19]
Heinrich et al.

[11] Patent Number: 6,110,698
[45] Date of Patent: Aug. 29, 2000

[54] SCREEN FOR ULTRASPIRACLE INHIBITORS

[75] Inventors: Julia N. Heinrich, Princeton, N.J.; Fernando Dela E. Cruz, Fairless Hills, Pa.; Donald R. Kirsch, Princeton, N.J.

[73] Assignee: American Cyanamid Company, Madison, N.J.

[21] Appl. No.: 08/865,960

[22] Filed: May 30, 1997

Related U.S. Application Data

[60] Provisional application No. 60/108,817, May 31, 1996.

[51] Int. Cl.[7] .............................. C12Q 1/02; C12N 15/63; C12N 15/81; C12N 15/00
[52] U.S. Cl. ................................. 435/29; 435/7.1; 435/4; 435/69.1; 435/325; 435/375; 435/255.1; 435/320.1; 530/350; 536/23.1
[58] Field of Search .................................. 435/29, 7.1, 4, 435/69.1, 325, 375, 255.1, 320.1; 530/350; 536/23.1

[56] References Cited

U.S. PATENT DOCUMENTS

| | | | |
|---|---|---|---|
| 5,514,578 | 5/1996 | Hogness et al. | 435/240.2 |
| 5,639,616 | 6/1997 | Liao et al. | 435/7.1 |
| 5,641,652 | 6/1997 | Oro et al. | 435/69.1 |
| 5,861,274 | 1/1999 | Evans et al. | 435/69.1 |

OTHER PUBLICATIONS

International Preliminary Examination Report dated Mar. 30, 1998 received in the corresponding international application.
Richards, Biol. Rev. 56:501, 1981.
Ashburner et al., Cold Spring Harbor Symp. Quant. Biol. 38:655, 1974.
Kerkut et al., Comprehensive Insert Physiology, Biochemistry and Pharmacology: Endocrinology I vol. 7,364, 1985.
Wing, Science 241:467, 1988.
Yund et al., Proc. Natl. Acad. Sci. USA 17:6039, 1978.
Salerno et al., Nuc. Acids. Res. 24:566, 1996.
Christian et al., Biochem. Biophy. Res. Comm. 193:1318, 1993.
Cherbas et al., Proc. Natl. Acad. Sci. USA 85:2096, 1988.
Oro et al., Develop 115: 446, 1992.
Perrimon et al., Genetics 111: 23, 985.
Garen et al., Proc. Natl. Acad. Sci. USA 74: 5099, 1977.
Segraves, Rec. Prog. Horm. Res. 49: 167, 1994.
Henrich et al., Nucl. Acid. Res. 18: 4143, 1990.
Shea et al., Genes Dev. 4: 1128, 1990.
Yao et al., Cell 71: 63, 1992.
Yao et al., Nature 366: 476, 1993.
Zelhof et al., Proc. Natl. Acad. Sci. USA 92: 10477, 1995.
Zelhof et al., Mol. Cell Biol. 15: 6736, 1995.
Sutherland et al., Proc. Natl. Acad. Sci. USA 92: 7966, 1995.
Graf, Parasitology Today 9: 471, 1993.
Koelle et al., Cell 67: 59, 1990.
Talbot et al., Cell 73: 1323, 1993.
Mangelsdorf et al, Cell 83: 841, 1995.
Dana et al., Mol. Endocrinol. 8: 1193, 1994.
Guthrie et al., Meth. Enzymol. vol. 194, 1991.
Prasher, Trends Gen. 11: 320, 1995.
Hills et al., Yeast 2: 163, 1986.
Bai et al., Vitamins Horm. 51: 289, 1995.
Blondelle et al., TibTech 14: 60, 1996.
McDonnell et al., Mol. Cell. Biol. 9: 3517, 1989.
Mak et al., J. Biol. Chem. 264: 21613, 1989.
Mak et al., Rec. Prog. Horm. Res. 49: 347, 1994.
He et al., Biochem. Bioph. Res. Comm. 171: 697, 1990.
Mak et al., Gene, 145: 129, 1994.
Khoury Christianson et al., Proc. Natl. Acad. Sci. USA 89: 11503, 1992.
Hoffmann, J. Biol. Chem. 260: 11831, 1985.
Broach et al., Gene 8: 121, 1979.
Oro et al., Nature 347: 298, 1990.
Talbot et al., "Drosophilia Tissues with Different Metamorphic Responses to Ecdysone Express Different Ecdysone Receptor Isoforms," *Cell*, vol. 73, pp. 1323–1337, 1993.
Mangelsdorf et al., "The RXR Heterodimers and Orphan Receptors," *Cell*, vol. 83, pp. 841–850, 1995.
Oro et al., "Relationship between the product of the *Drosophilia ultraspiracle* locus and the vertebrate retinoid X receptor," *Nature*, vol. 347, pp. 298–301, 1990.

*Primary Examiner*—Elizabeth Kemmerer
*Assistant Examiner*—Nirmal S. Basi
*Attorney, Agent, or Firm*—Darby & Darby

[57] ABSTRACT

This invention discloses methods for identifying compounds, variant nuclear proteins and other auxiliary proteins that interfere with the Drosophila ultraspiracle protein ("Usp") and homologs thereof. The methods disclosed involve transformed yeast cells which contain a Usp binding partner, Usp or a homolog thereof which can bind with the Usp binding partner, and a reporter gene which requires a functional Usp—Usp binder partner complex for expression. The transformed yeast cells are incubated in the presence of a test compound to form a test culture and in the absence of a test compound to form a control culture. The expression of the reporter gene is monitored in one example by exposing the test and control cultures to canavanine under conditions in which control cultures exhibit reduced growth and detecting test cultures in which growth is increased relative to growth of control cultures.

9 Claims, 2 Drawing Sheets

FIG. 1

| | A/B | C | D | E | F | |
|---|---|---|---|---|---|---|
| USP | 1 — 106 | 171 — 226 | | 510 | | |
| EcR | A/B — 263 | C 329 | D 430 | E 651 | F 878 | |
| EcRΔA/B | — 69 | C 170 | D 391 | E 618 | | |
| mAR | A/B — 535 | 600 | 680 | 899 | | |
| EcR\mAR-DE | A/B — 263 | C 361 | D 432 | E 651 | | |
| mAR\EcR-DEF | A/B — 535 | 606 | 679 | 900 | F 1127 | |
| mAR\EcR-EF | A/B — 535 | 600 | 680 | 904 | F 1131 | |
| mAR\EcR-E | A/B — 535 | 600 | 680 | 914 | | |
| mAR\EcR-DEF | A/B — 535 | 600 | 680 | 753 — 974 | F 1201 | |
| mAR\EcR-CDEF | A/B — 541 | 607 | 708 | 928 | F 1156 | |

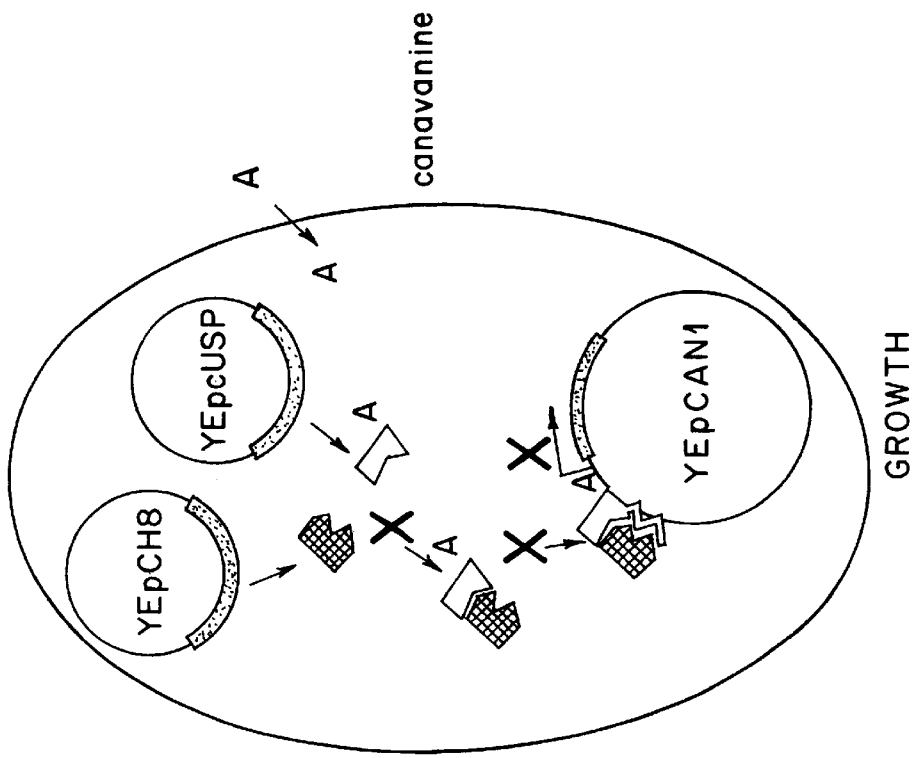
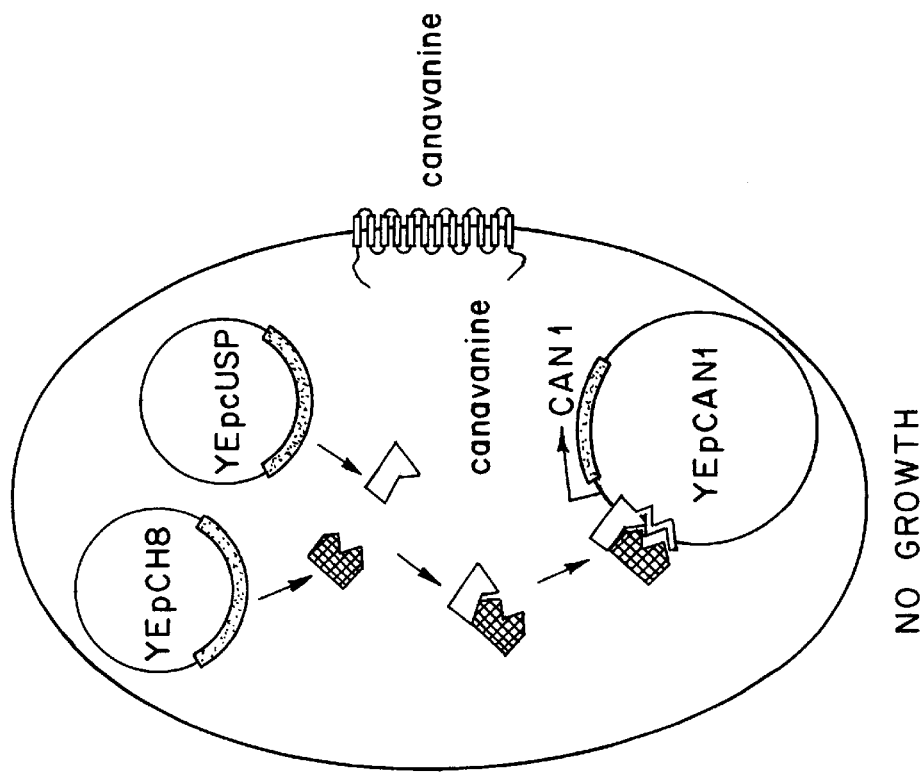
FIG. 2A
FIG. 2B

SCREEN FOR ULTRASPIRACLE INHIBITORS

This application is based upon a Provisional Patent Application, Serial No. 60/108,817 filed May 31, 1996. Applicants claim the benefit of the filing date of the aforesaid Provisional application under 35 U.S.C. 119.

FIELD OF THE INVENTION

This invention relates to the identification of inhibitors of "orphan" nuclear receptors (i.e., receptors for which no natural ligand is known). The invention relates to the Ultraspiracle protein (Usp) of *Drosophila melanogaster* and homologues thereof in other insect species. The invention provides methods for identifying compounds, variant nuclear proteins, and other auxiliary proteins that interfere with Usp function. USP inhibitory compounds are useful as insecticides or as lead compounds for the development of insecticides.

BACKGROUND OF THE INVENTION

The ultraspiracle (Usp) gene of *Drosophila melanogaster* encodes a protein that is required throughout the development of flies (Oro et al., *Develop.* 115:449, 1992). It was first identified by the phenotype of mutants that died in the molting process between the first and second instar stages and thus had two sets of spiracles (Perrimon et al., *Genetics* 111:23, 1985). The behavior of these mutants suggested that Usp functions in the ecdysone (Ec) response pathway of metamorphoses and imaginal disk formation. It has subsequently been found that Usp also functions in female reproduction and eye morphogenesis, and may participate in Ec-dependent and Ec-independent processes in the fly. (Garen et al., *Proc.Natl.Acad.Sci.USA* 74:5099, 1977; Segraves, *Rec.Prog.Horm.Res.* 49:167, 1994).

Cloning the Usp gene revealed sequence homology between Usp and the vertebrate retinoic acid X receptors (RXRs) (80% identity in the DNA binding domain and 49% in the hormone binding domain) (Henrich et al., *Nuc.Acids.Res.* 18:4143, 1990; Shea et al., *Genes Dev.* 4:1128, 1990; Oro et al., *Nature* 347:298, 1990). This relationship led to the elucidation of the following properties of Usp: (i) Usp can functionally substitute for RXR in dimerizing with the vertebrate nuclear receptors thyroid hormone receptor (TR), vitamin D receptor (VDR), and peroxisome proliferator-activated receptor (PPAR) (Yao et al., *Cell* 71:63, 1992); (ii) Usp cannot bind or respond to retinoic acid ligands (Yao, 1992, supra; (iii) Usp heterodimerizes with the ecdysone receptor (EcR) and thereby confers on EcR the ability to mediate ecdysone responses (Oro et al., *Develop.* 115:449, 1992; Yao et al., *Cell* 71:63, 1992; Yao et al., *Nature* 366:476, 1993); (iv) The ability of the EcR/Usp complex to mediate ecdysone responses can be repressed by three other Drosophila hormone orphan receptors (DHRs): DHR78, DHR38, and sevenup (svp) (Zelhof et al., *Proc.Natl.Acad..Sci.USA* 92:10477, 1995; Zelhof et al., *Mol.Cell.Biol.* 15:6736, 1995; Sutherland et al., *Proc.Natl.Acad.Sci.USA* 92:7966, 1995); and (v) DHR38 competes with EcR for heterodimerization with Usp and thereby promotes dissociation of the EcR/Usp heterodimer (Sutherland et al., *Proc.Natl.Acad.Sci.USA* 92:7966, 1995). These properties indicate that the Usp-RXR system has been evolutionarily conserved; that Usp, similar to RXR, may use heterodimerization as a mechanism to coordinate the function of multiple signal transduction pathways; and that Usp and RXR are functionally distinct.

These properties of Usp implicate it as an important target for insecticides. In particular, the role of Usp in insect development, and the differences between Usp and vertebrate RxR proteins, implicate it as a target for environmentally safe compounds that act as insect growth regulators (IGRs) (Graf, *Parasitology Today* 9:471, 1993). Thus, there is a need in the art for compositions and methods useful for identifying compounds that selectively interfere with the function of Usp.

SUMMARY OF THE INVENTION

The present invention provides a method for identifying mediators of the transcriptional activity of "orphan" nuclear receptors, i.e., receptors for which no natural ligand has been identified. In one aspect, the invention provides a method for identifying compounds that inhibit the function of Drosophila ultraspiracle protein (Usp). The method comprises:

(i) providing a transformed yeast cell comprising:
(a) a Usp binding partner;
(b) Usp or derivatives thereof capable of forming a functional complex with the binding partner; and
(c) a reporter gene, wherein expression of the reporter gene requires the Usp—Usp binding partner complex;

(ii) incubating the transformed yeast cell in the presence of a test compound to form a test culture, and in the absence of a test compound to form a control culture;

(iii) monitoring expression of the reporter gene in the test and control cultures; and (iv) identifying as a compound that inhibits the function of Usp any compound that detectably reduces the expression of the reporter gene in the test culture relative to the control culture.

In a preferred embodiment, a *S. cerevisiae* cell is provided that expresses Usp and a Usp binding partner comprising mAR\EcR-CDEF. The cell also contains a reporter gene comprising an ecdysone response element operatively linked to DNA encoding arginine permease (the CAN1 gene product). The reporter gene is transcriptionally activated only in the presence of a functional complex between Usp and mAR\EcR-CDEF; as a consequence, the cell expresses CAN1 and is sensitive to the toxic (growth-inhibitory) action of canavanine (an arginine analogue). When the cell is exposed to a Usp inhibitor compound, transcriptional activation of the reporter gene ceases, CAN1 is no longer expressed, and the cell is able to grow in the presence of canavanine. In this manner, a large number of compounds can be screened for Usp inhibitor activity in a high-throughput mode.

In general, modulators of transcriptional activity of a nuclear receptor are identified according to the present invention by contacting the receptor with a binding partner with which it forms a heterodimer, wherein the heterodimer interacts with, and transcriptionally activates, a known DNA response element in a hormone-independent manner. By monitoring the transcriptional activation of a suitable reporter gene, different classes of modulators (e.g., compounds, variant receptors, auxiliary proteins) can be identified.

BRIEF DESCRIPTION OF THE DRAWINGS

FIG. 1 is a schematic representation of native and recombinant nuclear receptors: Ultraspiracle protein (Usp); Ecdysone receptor (EcR); mammalian androgen receptor (mAR); N-terminal truncated EcRΔA/B; and recombinant chimeras. The recombinant proteins are depicted according to the standard designation of functional domains A through F and are aligned by domain C.

FIGS. 2A and 2B are schematic representations of the method for identifying Usp inhibitors according to the present invention. A can1 yeast strain contains three plasmids: YEpcUsp expresses Usp; YEpmAR\EcR-CDEF expresses mAR\EcR-CDEF; and YEpCAN1 expresses canavanine permease (CAN1) under the control of the ecdysone response element (EcRE$_2$). In FIG. 2A, co-expression of Usp and mAR\EcR-CDEF results in the expression of CAN1 and growth repression by canavanine. In FIG. 2B, an inhibitor (1) of Usp interferes with the expression of canavanine permease and allows growth even in the presence of canavanine.

DETAILED DESCRIPTION OF THE INVENTION

The present invention includes methods and compositions for identifying compounds that inhibit the functions of Drosophila ultraspiracle protein (Usp) as well as those of Usp homologues in other insect species. In a preferred method, a yeast cell is provided that comprises: (a) a Usp binding partner; (b) Usp or derivatives thereof capable of forming a functional complex with the binding partner; and (c) a reporter gene, which requires for its expression a functional Usp—Usp binding partner complex. The yeast cell is incubated in the absence and presence of test compounds that are being evaluated for their ability to interfere with Usp function, and the resulting cultures are monitored for expression of the reporter gene. Usp-inhibitory compounds are identified as those compounds that reduce the expression of the reporter gene in treated cultures relative to control cultures (including untreated cultures and wild-type cultures).

The methods of the present invention can be used to identify compounds that inhibit the function of a nuclear hormone receptor, even when the natural ligand of the receptor is not known (i.e., "orphan" receptors). This is achieved by providing a cell, preferably a yeast cell, which expresses the receptor and a suitable reporter gene and in which the reporter gene is transcriptionally activated by the receptor in a ligand-independent manner. If required to achieve ligand-independent transcriptional activation of the reporter gene, a heterodimeric binding partner of the receptor is co-expressed in the same cell.

Usp is encoded by an open reading frame of 1527 nucleotides and is a polypeptide of 508 amino acids having a molecular mass of 55,252 daltons (Henrich et al., *Nuc.Acids.Res.* 18:4143, 1990; Shea et al., *Genes Dev.* 4:1128, 1990; Oro et al., *Nature* 347:298, 1990). Usp has an apparent domain structure typical of the nuclear steroid receptor family, including an A/B (transactivation) domain, a C (DNA binding/dimerization/transactivation) domain, a D (nuclear localization) domain, and an E (dimerization) domain. In practicing the present invention, any derivative of Usp may be used that is capable of forming a functional complex with a Usp binding partner. A "functional Usp—Usp binding partner complex" as used herein is a complex that interacts productively with a cognate DNA transcriptional activation sequence (specified by the Usp binding partner) so as to activate transcription of DNA sequences located downstream of the transcriptional activation sequence. Useful Usp derivatives may include Usp polypeptides in which one or more amino acids have been added or deleted relative to the wild-type sequence, or in which one or more amino acids have been replaced with different amino acids that do not affect the formation of a functional Usp—Usp binding-partner complex. Furthermore, the methods of the present invention can be used to screen Usp mutants or derivatives to identify those that retain their ability to form a functional Usp—Usp binding partner complex.

Binding partners of Usp or of orphan receptors encompass native and recombinant polypeptides that form functional complexes with Usp or with other orphan receptors. Usp binding partners according to the present invention include without limitation ecdysone receptor (EcR), which comprises three isoforms: ECR-A, ECR-B1, and EcR-B2 (Koelle et al., *Cell* 67:59, 1990; Talbot et al., *Cell* 73:1323, 1993); and the vertebrate receptors TR, VDR, and PPAR (Yao et al., *Cell* 71:63, 1992). Useful binding partner derivatives include those in which one or more amino acids have been added or deleted relative to the wild-type sequence, or in which one or more amino acids have been replaced with different amino acids that do not affect the formation of a functional Usp—Usp binding-partner complex. Chimeras between different nuclear receptor proteins, such as, for example, between Drosophila nuclear receptor proteins known to bind Usp and other, non-Drosophila members of the steroid receptor polypeptide family, are also included. In a preferred embodiment, the Usp binding partner comprises a chimera comprising the A/B domain of a mammalian androgen receptor and the C,D,E, and F domains of EcR.

Reporter genes useful in practicing the present invention include genes (i) that are transcriptionally activated by a Usp—Usp binding partner complex; and (ii) whose expression in yeast is readily detectable. Typically, a reporter gene comprises at least two DNA sequence components, which are operably linked to each other: (i) a 5' regulatory region, including promoter elements and elements responsive to the particular Usp—Usp binding partner complex employed; and (ii) a 3' protein-coding region encoding a reporter polypeptide. These two sequence components may additionally be separated by sequences encoding a 5'-untranslated region of the messenger RNA, including sequences that function in initiation of protein synthesis. Furthermore, the protein-coding sequence of the reporter polypeptide may be flanked on its 3' terminus by a polyadenylation consensus sequence, transcription termination sequence, and the like.

Examples of suitable regulatory regions include without limitation those comprising an ecdysone response element (ERE), androgen response element (ARE), Vitamin D response element (VRE), retinoic acid response element (RRE), thyroid hormone response element (THRE), chicken ovalbumin upstream transcription factor response element (COUP-TE), and peroxisome proliferator-activated response element (PPAP-RE). It will be understood that the sequence of a particular response element may be truncated, multimerized, combined with other response elements, mutated, covalently modified, placed at varying distances upstream of the reporter polypeptide coding sequence, and otherwise manipulated, so long as the resulting response element sequence as a whole confers on the reporter gene the capacity to be transcriptionally activated by the particular Usp—Usp binding partner complex employed, i.e., the reporter gene comprises a functional response element. (Mangelsdorf et al., *Cell* 83:841, 1995; Dana et al., *Mol.Endocrinol.*8:1193, 1994).

Examples of suitable reporter polypeptides include without limitation: β-galactosidase derived from *E. coli* (LacZ); arginine permease derived from *S. cerevisiae* (CAN1); polypeptides involved in nucleoside and amino acid metabolism, such as the products of the URA3, LEU2, LYS2, HIS3, HIS4, TRP1, and ARG4 genes; polypeptides that confer resistance to drugs such as hygromycin, tunicamycin, cycloheximide, and neomycin; and green fluorescence protein (GFP) (Guthrie et al., *Meth.Enzymol.* Vol. 194, 1991; Prasher, *Trends Gen.* 11:320, 1995). Detection of expression of the reporter gene (i.e., as reflected in synthesis of the reporter polypeptide) may be achieved using any means known in the art, including without limitation enzymatic assays, growth assays, immunoassays, ligand binding assays, drug resistance assays, fluorescence assays, and the like. Preferably, in the absence of a functional Usp—Usp binding partner complex, transcription of the reporter gene occurs at a level that is low enough so that it is either undetectable in the assay employed, or can be readily distinguished in such an assay from the transcription that occurs in the presence of Usp—Usp binding partner complex. Reporter gene expression in the presence of a functional Usp—Usp binding partner complex may confer a positive or negative trait on the transformed yeast cell. In a preferred embodiment, yeast comprising both a functional Usp—Usp binding partner complex and an appropriate reporter gene exhibit poor growth and growth is restored in the presence of an inhibitor of Usp function.

In practicing the present invention, many conventional techniques in molecular biology, microbiology, recombinant DNA, and protein biochemistry are used. Such techniques are well known and are explained fully in, for example, Sambrook et al., 1989, *Molecular Cloning: A Laboratory Manual,* Second Edition, Cold Spring Harbor Laboratory Press, Cold Spring Harbor, New York; *DNA Cloning: A Practical Approach,* Volumes I and II, 1985 (D. N. Glover ed.); *Oligonucleotide Synthesis,* 1984, (M. L. Gait ed.); *Transcription and Translation,* 1984 (Hames and Higgins eds.); *A Practical Guide to Molecular Cloning;* the series, *Methods in Enzymology* (Academic Press, Inc.); and *Protein Purification: Principles and Practice,* Second Edition (Springer-Verlag, N.Y.).

In practicing the present invention, any suitable recombinant cloning vectors may be used for introducing into yeast DNA sequences encoding Usp and Usp binding partners, as well as DNA sequences comprising reporter genes. Such vectors will often include one or more replication systems for cloning or expression, one or more markers for selection in the host, e.g. prototrophy or antibiotic resistance, and one or more expression cassettes. The inserted sequences may be synthesized by standard methods or isolated from natural sources. Suitable vectors include without limitation YEp and YIp vectors (Hill et al., *Yeast* 2:163, 1986). Non-limiting examples of yeast promoters that may be present in these vectors to direct the expression of Usp and Usp binding partners include metallothionein promoter (CUP1), triosephosphate dehydrogenase promoter (TDH3), 3-phosphoglycerate kinase promoter (PGK), glyceraldehyde-3-phosphate dehydrogenase (GAPDH) promoter, galactokinase (GAL1) promoter, galactoepimerase promoter, and alcohol dehydrogenase (ADH) promoter.

Host yeast cells may be transformed by any suitable method, including without limitation methods that employ calcium phosphate, lithium salts, electroporation, and spheroplast formation (Sherman et al., *Methods in Yeast Genetics,* Cold Spring Harbor Laboratory, 1982). Suitable host cells include without limitation *Saccharomyces cerevisiae* and *Schizosaccharomyces pombe.* Any host cell in which ligand-independent activity of a Usp—Usp binding partner can be measured may be used in practicing the invention. Host cells may also be modified or manipulated with respected to their ability to produce different types of covalent modification of proteins, such as, e.g., phosphorylation (Bai et al., *Vitamins Horm.* 51:289, 1995).

Yeast cells comprising Usp, a Usp-binding partner, and an appropriate reporter gene are used in an assay to identify compounds that interfere with Usp function. Typically, the cells are incubated under conditions in which Usp and a Usp binding partner are expressed and form functional complexes, resulting in expression of the reporter polypeptide. Cultures expressing Usp, Usp binding partner and reporter polypeptides are incubated in the presence of test compounds to form test cultures, and in the absence of test compounds to form control cultures. Incubation is allowed to proceed for a sufficient time and under appropriate conditions to allow for interference with Usp function and turnover of pre-existing reporter polypeptides. At a predetermined time after the start of incubation with a test compound, an assay is performed to monitor the level and/or activity of the reporter polypeptide. Additional controls, with respect to both culture samples and assay samples, are also included, such as, for example, wild-type yeast and yeast expressing a functional CAN1 gene product. Usp inhibitory compounds are identified as those that reduce the expression of the reporter gene in the test cultures relative to the control cultures.

Without wishing to be bound by theory, it is contemplated that useful Usp inhibitory compounds identified by the methods of the present invention will be those that interfere with any of the following: (a) the formation of a functional Usp—Usp binding partner complex; (b) the interaction of an agonist with the Usp—Usp binding partner complex; or (c) the functional interaction of the Usp—Usp binding partner complex with the cognate DNA response element that is normally transcriptionally activated by a native Usp—Usp binding partner complex.

Preferably, the methods of the present invention are adapted to a high-throughput screen, allowing a multiplicity of compounds to be tested in a single assay. Such inhibitory compounds may be found in, for example, natural product libraries, fermentation libraries (encompassing plants and microorganisms), combinatorial libraries, compound files, and synthetic compound libraries. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., *TibTech* 14:60, 1996). Usp inhibitor assays according to the present invention are advantageous in accommodating many different types of solvents and thus allowing the testing of compounds from many sources.

Once a compound has been identified by the methods of the present invention as a Usp inhibitor, different in vivo and in vitro tests may be performed to further characterize the nature and mechanism of the Usp inhibitory activity. For example, the compound may be tested for Usp inhibitory activity in a cell expressing, in addition to Usp, a different Usp binding partner and reporter gene than was present in the cell in which the inhibitory activity of the compound was originally detected. Inhibitory activity may be tested in vitro by monitoring the ability of the compound to inhibit heterodimeric complex formation between Usp and the Usp binding partner and/or complex formation between the Usp—Usp binding partner complex and DNA containing the appropriate response element; this may be achieved using, e.g., glycerol gradient fractionation, gel shift assays, and protease protection assays.

Compounds identified as Usp inhibitors may be modified to enhance potency, efficacy, uptake, stability, and suitability for use in commercial insecticide applications, etc. These modifications are achieved and tested using methods well-known in the art.

Insecticide compositions

Usp inhibitory compounds according to the present invention encompass "insect growth regulators" (IGRs) that selectively inhibit insect development without affecting vertebrate animals or plants. Accordingly, it is believed that such compounds are particularly suitable for use as insecticides, since they are expected to be environmentally benign.

The insecticide activity of Usp inhibitors identified using the methods of the present invention is tested using techniques well-known in the art. For example, formulations of each identified compound (see below) may be sprayed on a plant to which insect larvae are then applied; after an appropriate time, the degree of plant destruction by the larvae is quantified.

For use as insecticides, Usp inhibitory compounds are formulated in a biologically acceptable carrier. Suitable biologically acceptable carriers include, but are not limited to, phosphate-buffered saline, saline, deionized water, or the like. Preferred biologically acceptable carriers are physiologically or pharmacologically acceptable carriers.

The insecticide compositions include an insecticide effective amount of active agent. Insecticide effect amounts are those quantities of the insecticide agents of the present invention that afford prophylactic protection against insect infestation in plants and animals, and which result in amelioration or cure of an existing insect infestation in plants or animals. This insecticide effective amount will depend upon the target insect, the agent, and the host. The amount can be determined by experimentation known in the art, such as by establishing a matrix of dosages and frequencies and comparing a group of experimental units or subjects to each point in the matrix.

For agricultural use, the insecticide active agents or compositions can be formed into dosage unit forms such as, for example, emulsifiable concentrates (EC), suspension concentrates (SC), and water dispersable granules (WDG). For pharmaceutical use, the insecticide active agents or compositions can be formed into dosage unit forms such as for example, creams, ointments, lotions, powders, liquids, tablets, capsules, sprays, or the like. If the insecticide composition is formulated into a dosage unit form, the dosage unit form may contain an insecticide effective amount of active agent. Alternatively, the dosage unit form may include less than such an amount if multiple dosage unit forms or multiple dosages are to be used to administer a total dosage of the active agent. Dosage unit forms can include, in addition, one or more excipient(s), diluent(s), disintegrant(s), lubricant(s), plasticizer(s), colorant(s), dosage vehicle (s), absorption enhancer(s), stabilizer(s), bactericide(s), or the like.

The insecticide agents and compositions of the present invention are useful for preventing or treating insect infestations in plants and animals. Prevention methods incorporate a prophylactically effective amount of an insecticide agent or composition. A prophylactically effective amount is an amount effective to prevent infestation and will depend upon the insect, the agent, and the host. These amounts can be determined experimentally by methods known in the art and as described above. Treatment methods incorporate a therapeutically effective amount of an insecticide agent or composition. A therapeutically effective amount is an amount sufficient to reduce an insect infestation. This amount also depends upon the target insect, the agent, and the host, and can be determined as explain above.

The prophylactically and/or therapeutically effective amounts can be administered in one administration or over repeated administrations. Therapeutic administration can be followed by prophylactic administration, once the initial insect infestation has been resolved.

The insecticide agents and compositions can be applied to plants topically or non-topically, i.e., systemically. Topical application is preferably by spraying onto the plant. Systemic administration is preferably by foliar application or by application to the soil and subsequent absorption by the roots of the plant.

DESCRIPTION OF THE PREFERRED EMBODIMENTS

The following examples illustrate the invention without limitation.

EXAMPLE 1

Cloning of Usp and Usp Binding Partners and Construction of a Reporter Gene

A. Construction of Expression Plasmids

The methods used for manipulating DNA and yeast are those well-known in the art (Guthrie et al., *Meth.Enymol.* Vol. 194, 1991). DNA sequences encoding the N-terminal of the full length nuclear receptors and chimeras described below were fused in frame to the aminoterminus of the seventy-six amino acid ubiquitin (Ubi) in high-copy YEp yeast expression vectors (McDonnell et al., *Mol.Cell.Biol.* 9:3517, 1989; Mak et al., *J.Biol.Chem.* 264:21613, 1989; Mak et al. *Rec.Prog.Horm.Res.* 49:347, 1994). Upon transfection of each plasmid in yeast, a recombinant fusion protein is expressed, which is cleaved by an endogenous protease to release the mature nuclear protein or chimera shown in FIG. 1.

The YEpcUsp plasmid was constructed by amplifying the Usp gene in the pCFI plasmid (Shea et al., *Genes Dev.* 4:1128, 1990) as two PCR fragments and inserting them into the Eag I and Dra III sites of the multiple cloning sites, of the YEpcMCS.

The 5' half of Usp was amplified with the sense primer 5'-ACTTCACGGCCGATGGACAACTGCGACCAGGAC GCCA-3' (SEQ ID NO:1) containing at the 5' end Eag I and the antisense primer 5'-CACCTGGGCAAAGTGCGGCATCAT-3' (SEQ ID NO:2) containing at the 3' end BssH II. The 3' half of Usp was amplified with the sense primer 5'-CAAACAGCTCTTCCAGATGGTCGA-3' (SEQ ID NO:3) containing at the 5' end a BssH II site, and the antisense primer 5'-ACTACTCAAACAGTG CTACTCCAGTTTCATCGCCAGGCC-3' (SEQ ID NO:4) containing a Dra III site at the 3' end. The two PCR fragments and YEpcmcs were cleaved with Eag I and Dra III site, mixed and ligated together to obtain YEpcUSP. In YEpcUSP the copper-responsive yeast metallothionein promoter (CUP1) regulates the expression of Usp, and leucine (LEU) is the selectable marker.

The YEpEcRB1 plasmid was made in three steps. First, YEp was modified at the Afl II-Kpn I site by the addition of a double-stranded linker

```
5'-TTAAGACTAAGAGGTGGTATGAAGCGGCGCTGGTCGAACAACGGCGGCTTCAT    (SEQ ID NO:5)
    3'-CTGATTCTCCACCATACTTCGCCGCGACCAGCTTGTTGCCGCCGAAGTA    (SEQ ID NO:6)

GCCTACCGGAGGCGGCCGTCCGGACGGCCGGGTAC-3'
CGGATGGCCTCCGCCGGCAGGCCTGCCGGCC-5'
``` consisting of from the 5' end: an Afl II site, the sequences representing the 6 amino acids at the carboxyl terminal end of ubiquitin, the 5' sequences of the EcR gene up to the first EcoN I site and both a BspE I site and the Kpn I site at the 3' end, to obtain YEpBspE I. Second, a polymerase chain reaction (PCR) fragment was obtained using a pMKI plasmid containing the EcR-17 (Koelle et al., Cell 67:59, 1990) as template and the sense primer 5'-AGGAGATCTGGGACGTTCATGCCAT-3' (SEQ ID NO:7) containing a BspE I at the 5' end and the antisense primer 5'-TAAACGCGTTCCGGACTATGCAGTCGTCGA GTGCTCCGACTTAAC-3' (SEQ ID NO:8) containing both BspE I and Mlu I sites at the 3' end as primers. The resulting fragment was inserted into the Bgl I-Mlu I site of pMK1 to get pMK-EcR. Third, pMK-EcR was digested first with BspE I and then with EcoN I, the digest was resolved on a 1% agarose gel, and the 2.6 kb fragment of the EcR was excised, gel purified, and inserted into the EcoN I and BspE I sites of YEpBspE to obtain YEpEcR. In YEpEcR the expression of EcR is regulated by the yeast constitutive promoter triosephosphate dehydrogenase (TDH3), and tryptophan (TRP) is the selectable marker.

Plasmids YEpEcR-A and YEpEcR-B2 were made from YEpEcR-B1 by excising from YEpEcR-B1 an Afl II and Asc I fragment, and inserting in its place a PCR fragment that was identical to the original except for containing the unique sequences of EcR-A and EcR-B2: The templates were pWT57 and WT56 (Talbot et al., Cell, 73:1323(1993), respectively. The sense primers were 5'-CTTGTCTTAAGACTAAGAGGTGGCATGGATACT TGTGGATTAGT-3' (SEQ ID NO:9) and 5'-CTTGTCTTAAGACTAAGAGGTGGCATGTTGACG ACGAGTGGACA-3', (SEQ ID NO:10) respectively. The antisense primer 5'-GCACTCCTGACACTTTCGCCTCAT-3' (SEQ ID NO:11) was used for both reactions.

The YEpEcRΔA/B plasmid was made by excising from YEpEcR-B1 a BamH I and BspE I fragment containing the TDH3 promoter, the Ubi gene and the EcRΔA/B; and replacing it with both a fragment containing the TDH3 promoter, Ubi gene, and a novel Dra III site. The Dra III site resulted in an additional 9 bases downstream of the EcRΔA/B from the closest BspE I site. The reinserted fragment was made from two PCR fragments, the first PCR reaction amplified the TDH₃-Ubi portion of YEpecr with the sense primer 5'-ATGTGTCAGAGGTTTTCACCG-3' (SEQ ID NO:12) that included at the 5' end a BamH I site and the antisense primer 5'-TCATCACACGTGGTTGGCCAAGACAAG-3' (SEQ ID NO:13) which included at the 3' end a Dra III site; and the second PCR reaction amplified sequences downstream of the A/B domain of the EcR to BspEI site with the sense primer 5'-TCATCACACCACGTGGAGCTGTGCCTGGTTTGC GGCGAC-3' (SEQ ID NO:14), which contains a Dra III site at the 5' end, and the antisense primer 5'-CTCTCTTCAACCCACCAAAGGCCA-3' (SEQ ID NO:15), which contains BamH I site at the 3' end.

The YEpmAR5 plasmid (Mak et al., Rec.Prog.Horm.Res. 49:347, 1994) and either YEpEcR-B1 or YEpEcRΔA/B plasmids were used to make six chimeras (FIG. 1). The name of the chimeras begins with the nuclear receptor which contributes the N-terminal domain(s), followed by a slash "\", indicating the junction between two nuclear receptors, and ends with the name of the second nuclear receptor plus the domains which it contributes. All DNA base numbers are based on the numbers used in the gene sequences of EcR (Koelle et al., Cell 67:59, 1990) and mAR (He et al., Biochem.Bioph.Res.Comm. 171:697, 1990) and therefore, base number 1 is not the A in the initiation codon of the ORF. To obtain +1 of the A in the ATG of the ORF subtract 1067 from the EcR sequences and 32 from the mAR sequences.

The first chimera, YEpEcR\mAR-DE, was made in two steps. First, the EcRB1 gene was digested with Sac I and BspE I to excise bases 2151 to 3706 and retain the sequences composing the A/B and C regions and one-third of the D region. Second, the sense primer 5'-CATCATGAGCTCTCGTAAGCTGAAGAAACTTGGA AATCT-3' (SEQ ID NO:16) and the antisense primer 5'-CATCTTCTCCGGATCACTGTGTGTGGAAATAGAT GGGCT-3' (SEQ ID NO:17) were used (with the mAR5 gene as a template) to amplify the androgen receptor gene from bases 1856 to 2732, representing regions D and E, and a 0.9 kb fragment having Sac I and BspE I ends was obtained. After digestion with the respective restriction enzymes, the mAR fragment was cloned into the Sac I and BspE I sites of YEpEcR prepared previously.

The second chimera, YEpmAR\EcR-DEF, was made with Dra III and BssH II linkers inserted into the Sac I and BspE I sites, respectively, of YEpEcRB1. The resulting plasmid was then cut with Dra III and BssH II to release the 1.8 kb DNA fragment from bases 2151 to 3706 encoding two-thirds of the D region and all of the E and F regions. This fragment was isolated and cloned into the Dra III and BssH II sites of YEpmAR5 (Mak et al. Rec.Prog.Horm.Res. 49:347, 1994) which contain bases 33 to 1850 of the mAR. Both sites are present at the 3' end of the truncated mAR. The resulting protein expressed contains the A, B and C regions of the mAR and the D, E and F regions of EcR.

The third chimera, YEpmAR\EcR-EF, was made by amplifying from the EcRB1 bases 2358 to 2306 with the sense primer 5'-CATGATCACACAGTGCAGOAT GTATGAGCAGCCATCT-3' (SEQ ID NO:18) and antisense primer 5'-GATCTAGCGCGCCTATGCAGTCGTC GAGTGCTCCGA-3' (SEQ ID NO:19), obtaining a 1.3 kb fragment encoding the E and F regions of EcR and including Dra III and BssH II ends, respectively, digesting the PCR product with the appropriate enzymes, and cloning it into the Dra III and BssH II sites of YEpmAR6. YEpmAR6 contains a truncated mAR gene from bases 33 to 2072 and expresses a portion of the androgen receptor encoding the A, B, C and D regions.

The fourth chimera, YEpEcR\mAR-DE, was cloned according to the procedure for the third chimera (YEpmAR\EcR-E&F), except that the antisense primer used for the EcR gene was 5'-GATCTAGCGCGCCTAAAGGT GCGACTGGACCGATGG-3' (SEQ ID NO:20), and a 0.6 kb fragment containing bases 2358 to 3057 and encoding only the E and F region of the EcR was obtained.

The fifth chimera, YEpmAR-D\EcR-DEF, was cloned according to the procedure used for the second chimera (YEpmAR\EcR-DEF), except that the 1.8 kb fragment from bases 2151 to 3706 (encoding the D, E and F regions of the EcR) was cloned into the Dra III and BssH II sites of YEpmAR6.

The sixth chimera, YEpmAR\EcR-CDEF, was made by inserting into the Dra III site of YEpEcRΔA/B a PCR product made from YEpmAR using the sense primer 5'-TCATCACACCACGTGATGGAGGTGCAGTTAGGG CTGGGA-3' (SEQ ID NO:21) containing from the 5' end a Dra III site followed by the mAR gene from the first translational start ATG site; and the antisense primer 5'-TCATCACACGTGGTGGGTCTTCTGGGGTGGAAA GTAATA-3', (SEQ ID NO:22) that encodes a Dra III site at the 3' end along with sequences of the A/B domain mAR gene.

The plasmid YEpV3 is disclosed in McDonnell et al., *Md. Cell Biol*, 9:3517, 1989; and the plasmid YEpRXRα is disclosed in Mak et al., *Gene*, 145:129, 1994. Expression of Usp and RXRα is driven by the copper-responsive yeast metallothionein promoter (CUP1), and the selectable markers are leucine (LEU2) and tryptophane (TRP1), respectively. Expression of the EcR's, the chimeras, and VDR are regulated by the yeast constitutive triosephosphate dehydrogenase (TDH3) and tryptophane (TRP1) serves as a selectable marker.

B. Construction of reporter plasmids

The Usp reporter plasmid YEp-UspRE$_2$-LacZ was constructed by replacing in YEpEcRE$_2$-LacZ the EcR response element (EcRE$_2$) with two copies of a putative Usp response element (UspRE$_2$). The UspRE$_2$ corresponded to the sequence from −64 to −44 of the chorion s15 promoter (Shea et al., *Genes Dev.* 4:1128, 1990;Khoury Christianson et al., *Proc.Natl.Acad.Sci.USA* 89:11503, 1992) and it was constructed by synthesizing the oligonucleotide pair 5'-TCGAGTAGGTCACGTAAATGTCCA-3' (SEQ ID NO:23), and 3'-CATCCAGTGCATTTACAGGTCCGAGCT-5' (SEQ ID NO:24), which contained from the 5' to 3' ends of each sequence: 5 nucleotides for an Xho I site, followed by 21 bases of the putative Usp binding site and a single cytosine to complete the Xho I overhang.

The EcR response reporter plasmid (Koelle et al., *Cell* 67:59, 1990) YEpEcRE$_2$-LacZ was made as described (Mak et al., *J. Biol. Chem.*, 264:21613, 1989) and contained two copies of the EcRE in the Drosophila heat shock promoter 27 (hsp27), which were inserted into the Xho I site of pC2 and upstream of the yeast iso-1-cytochrome c promoter (CYC1) fused to the structural gene of *E. coli* LacZ (EcRE$_2$-LacZ), and has URA3 as the selectable marker (Mak et al., *J. Biol. Chem.*, 264:21613, 1989). The EcRE2 was constructed by synthesizing two oligonucleotides: 5'-TCGAGGACAAGTGCATTGAACCTGTCTCCGG GC-3' (SEQ ID NO:25), and 3'-CTGTTCACGTAACTTGGGAACAGAGGG CCCGAGCT-5' (SEQ ID NO:26), which contained the 23 bases of hsp27 followed by a Sma I site and ending at the 5' ends four nucleotides of compatible Xho I overhangs. The oligonucleotides were kinased, annealed together, and ligated into the reporter vector pC2 which had been previously digested with Xho I and dephosphorylated with calf intestinal alkaline phosphate. Both UspRE$_2$ and EcRE$_2$ were subjected to digestion with Sma I to show that they were inserted into the Xho I site, and to DNA sequencing analysis (Sequenase kit, Stratagene) to verify the presence of two copies of the element.

The YEp-VDRE$_2$ reporter plasmid was made by excising an Xho I fragment from YEpEcRE$_2$-LacZ and reinserting two copies of a 25 base pair sequence present in the human osteocalcin promoter (hOC) that was made from the oligonucleotide pair
5'TCGAGCTTACCGGGTGAACGGGGGCATTAC3' (SEQ ID NO:27)
3'CGAAGGCCCACTTGCCCCCGTAATGAGCT5' (SEQ ID NO:28)

The mAR response reporter plasmid YRpA$_2$ is disclosed in Mak et al., *Recent Prog. Horm. Res.*, 49:347, 1994.

The canavanine (CAN1) response reporter YEpEcRE$_2$-CAN1 was constructed from YEpEcRE$_2$-LacZ by excising the BamH I and Sac I portion containing the LacZ and reinserting a PCR product of CAN1. The PCR reaction contained as template genomic DNA from the wild type yeast strain S288C and primers made according to the sequence of CAN1 (Hoffmann, *J. Biol. Chem.*, 260:11831, 1985). The sense primer 5'-GTGCTC GGATCCATGACAAATTCAAAAGAAGACG-3' (SEQ ID NO:29) encodes a BamH I site followed by the 5' and of CAN1, and the antisense primer 5'-TGGTGGGAGCTCCTATGCTACAACATTCC-3' (SEQ ID NO:30) encodes the 3' and of the CAN1 gene followed by a Sac I site.

C. Yeast strains

Plasmid YEpUsp-LacZ was used in *S. cerevisiae* strain BJ2168, which has the genotype MATα leu2 trp1 ura3-52 prb1-1122 pep4-3 prc1-407 gal2. Plasmids YEpEcRE$_2$-CAN1, YEpEcRE$_2$-LacZ and YRpA$_2$ were used with the can1 deleted *S. cerevisiae* yeast strain CGY44(DC45), which has the genotype MATα ste11-Δ1 his4-519 leu2 trp1 ura3 can1-101.

EXAMPLE 2

Transcriptional Activation of Beta-Galactosidase Reporter Genes by Usp—Usp Binding Partner Complexes in Yeast The experiments described below were performed in order to quantify the ability of Usp—Usp binding partner complexes to activate transcription in *S. cerevisiae*.

METHODS:

Expression plasmids encoding Usp, Usp binding partners, and reporter genes constructed and transformed into yeast as described in Example 1 above. Where indicated, yeast were pretreated with 10 μM muristerone A or 1 μM testosterone. To prepare cytosolic extracts, cells were harvested by centrifugation, washed twice in water, and resuspended in Z buffer (60 mM Na$_2$HPO$_4$, 40 mM NaH$_2$PO$_4$, 10 mM KCl, 1 mM MgSO$_4$, 50 mM β-mercaptoethanol, pH 7.0). The cells were then lysed with 0.5 mm glass beads (Braun Instruments) by 5 cycles of vortexing (1 min each) followed by 1 min incubation on ice. The lysates were subjected to high-speed centrifugation to separate the particulate and supernatant fractions. The protein concentration of the supernatant (cytosolic extract) as determined by the Bradford assay (BioRad) was typically 5–10 mg/ml.

β-galactosidase activity was measured in a 1-ml reaction containing 800 μl Z buffer and 5–20 μg cytosolic extract. The reaction mixture was pre-incubated at 28° C. for 10 min, after which 200 μl of O-nitrophenyl galactopyranoside (4 mg/ml in water) was added, and incubation continued for an additional 10 min. The reaction was stopped by addition of 500 μl of 1M sodium carbonate. Finally, the absorbance of the reaction at 420 nm was measured using a spectrophotometer, and the values converted to Miller units per mg protein.

RESULTS:

To test whether nucleotides −64 and −44 of Drosophila follicular-specific chorion gene s15 can function as a cisbinding element for Usp, a duplicate copy of this sequence was inserted into a reporter plasmid that contains proximal promoter elements and the LacZ gene, and the resulting reporter plasmid YEpUspRE$_2$-LacZ was tested for β-galactosidase expression. Table 1 shows that all cytosolic extracts from BJ2168 yeast containing the reporter plasmid YEp-UspRE$_2$-LacZ had significant and similar levels of β-galactosidase activity, as compared to those with the control plasmid YEpcLacZ, which had undetectable levels (range of 1500 MU/mg compared with O MU/mg, respectively). The presence of Cu$^{2+}$, which induces expression of Usp from the copper-responsive metallothionein promoter (CUP1) copper promoter in YEpcUsp, had no effect. The results indicate that the YEp-UspRE$_2$-LacZ plasmid is constitutively active and is not further induced by the presence of Usp. Therefore, this reporter construct could not be used to assay Usp activity.

TABLE 1

| Reporter Plasmid | Usp Plasmid | Medium | 1β-Galactosidase (Mu/mg) |
|---|---|---|---|
| YEp-LacZ | – | – | 0 |
| YEp-LacZ | – | Cu$^{2+}$ | 0 |
| YEp-LacZ | + | – | 0 |
| YEp-LacZ | + | Cu$^{2+}$ | 0 |
| YEp-UspRE$_2$-LacZ | – | – | 1500 ± 157 |
| YEp-UspRE$_2$-LacZ | – | Cu$^{2+}$ | 1460 ± 199 |
| YEp-UspRE$_2$-LacZ | + | – | 1344 ± 142 |
| YEp-UspRE$_2$-LacZ | + | Cu$^{2+}$ | 1515 ± 220 |

The transcriptional activity of ECR-A or EcR-B2 was then tested using the reporter plasmid YEpEcRE$_2$-LacZ. The EcR isoforms differ in their N-terminal sequence; therefore, by domain swapping, the YEpEcR-B1 plasmid was modified to give aYEpEcR-A plasmid and a YEpEcR-B2 plasmid. The yeast strains were transformed with the appropriate combination of plasmids and tested for β-galactosidase activity. Table 2 shows that cytosolic extracts containing YEpEcRE$_2$-LacZ in the absence or presence of Usp had either undetectable or insignificant levels of β-galactosidase activities. These levels ranged from 0 to 132 MU/mg, and their mean (58) was defined as basal activity and used to determine the fold induction of activity. Cytosolic extracts containing an EcR isoform in addition to YEp-EcRE$_2$-LacZ exhibited significant levels of β-galactosidase activity, and the level was further increased for EcR-B1 and ECR-A containing cells by co-expression of Usp. Pretreatment of the yeast strains with the Ec agonist Muristerone A (Mur A) had no effect. The ability of Usp to increase the transcriptional activity of EcR-B1 four-fold, from 4103±709 MU/mg to 18007±1967 MU/mg, provided a significant Usp specific response. However, the Usp-independent activity of EcR was too high for use in an agar plate-based assay.

TABLE 2

| Nuclear Receptors | | β-Galactosidase Activity (Mu/mg) | | Induction | |
|---|---|---|---|---|---|
| Ecdysone Receptor | Usp | No Treatment | Muristerone A | Activity/Basal Activity* | Fold Activation by Usp |
| — | — | 23 ± 52 | 57 ± 69 | — | |
| — | Usp | 88 ± 64 | 63 ± 72 | | 1 |
| EcR-B1 | — | 4103 ± 709 | 4135 ± 716 | 71 ± 9 | |
| EcR-B1 | Usp | 18007 ± 1967 | 15691 ± 548 | 310 ± 34 | 4.4 ± 0.3 |
| EcR-A | — | 2523 ± 710 | 2890 ± 729 | 43 ± 13 | |
| EcR-A | Usp | 6694 ± 3187 | 6144 ± 2198 | 116 ± 37 | 3 ±0 1.5 |
| EcR-B2 | — | 480 ± 150 | 431 ± 107 | 8 ± 2 | |
| EcR-B2 | Usp | 459 ± 120 | 517 ± 3 | 6 ± 2 | 0.9 ± 1.5 |

*Basal Mean for all experiments is 58

The three isoforms share the carboxyl terminal 36 amino acids of their A/B domain and have different sequences at their N-terminal, being composed of 226, 197 and 17 amino acids for ECR-B1, ECR-A and EcR-B2, respectively. The results also show a decrease in both the level of the EcRs' constitutive activity, 4103±709 Mu/mg, 2523±710 MU/mg, and 480±150 MU/mg, respectively, and their enhancement by Usp, 4.4±0.3, 3.0±1.5, 0.9±1.5-fold induction, respectively. This suggested that the N-terminal domain of the EcR isoform determines both its independent constitutive activity as well as its inducibility by Usp.

On this basis, the N-terminal end of the EcR-B1 was deleted to determine if this domain was essential for transcriptional activity. A number of chimeras between the EcR-B1 and mAR were also made to obtain a form of the EcR which exhibits low basal activity and a pronounced Usp-inducible activity. All forms of the EcR were made by modifying the YEpEcR-B1 plasmid by substituting EcR sequences with the corresponding sequences from mAR present in YEpmAR. A schematic representation of the nuclear receptors used in this study are shown in FIG. 1. These are Usp, ECR-B1, mAR, and derivatives of EcR-B1 and mAR which include 1) an EcR truncated of its N-terminal or A/B domain (EcRΔA/B), 2) an EcR containing its own A/B, C and part of D domains with the remaining portion of domain D and domain E derived from the mAR (EcR\mAR-DE), 3) an EcR in which domains A/B and C come from mAR and D,E and F are from the EcR (mAR\ecr-DEF), 4) and EcR similar to mAR\EcR-DEF except in which domain D is also from the mAR (mAR\EcR-EF), 5) an EcR similar to mAR\EcR-EF but lacing domain F (mAR\EcR-E) 6) and EcR similar to mAR\EcR-DEF but in which domain D from the mAR was retained (mAR-D\EcR-DEF), and 7) an EcR in which the A/B domain of mAR is substituted for the A/B domain of the EcR (mAR\EcR-CDEF). High level expression of the recombinant proteins, except the mAR/EcR-CDEF chimera, in yeast extracts was confirmed in Western blots (data not shown).

Cytosolic extracts containing each form of the EcR with the appropriate reporter plasmid and containing or lacking Usp were assayed for β-galactosidase activity. Table 3 shows the results obtained for cells pretreated with either vehicle or a steroid: 10 μM Muristerone A (Mur A) or 1 μM testosterone. Since the E domain is typically the ligand binding domain of steroid/nuclear receptors, yeast cells containing nuclear receptors having domain E derived from EcR would be expected to respond to 10 μM Mur A, while those containing domain E from mAR would be expected to respond to 1 μM testosterone. In addition, domain C specifies the cis-DNA binding domain, and reporter genes were selected based on the origin of the domain C present in the chimeric receptor. That is, chimeras with domain C from EcR were tested with YEp-EcRE$_2$-LacZ, while chimeras with domain C from mAR were tested with YRpA$_2$-LacZ.

The low basal activity exhibited by mAR\EcR-CDEF results in high standard deviations and thus in a broad range of fold activation values. However, despite this variation with mAR\EcR-CDEF, the fold induction in the presence of Usp for all the inducible EcR forms is rather similar and within a 5 to 10 fold range (i.e., for AR\EcR-CDEF it ranges from 15±10 to 62.0±50, and for the others, not including EcR\mAR-DE strain pre-stimulated with testosterone, from

TABLE 3

| Nuclear Receptors | | β-Galactosidase Activity (Mu/mg) | | | | | |
|---|---|---|---|---|---|---|---|
| Ecdysone Receptor | | No Treatment | | Muristerone A | | Testosterone | |
| Chimera | Usp | Mu/mg | Usp (fold induction) | Mu/mg | Usp (fold induction) | Mu/mg | Usp (fold induction) |
| Receptors tested with the Drosophila Ecdysone receptor response element | | | | | | | |
| — | — | 0 | | 0 | | 0 | |
| — | Usp | 108 ± 11 | | 0 | | 0 | |
| EcR | — | 9946 ± 1661 | | 10315 ± 1777 | | 10230 ± 1880 | |
| EcR | Usp | 12256 ± 1385 | 1.2 ± 0.1 | 13134 ± 1268 | 1.4 ± 0.2 | 13100 ± 1773 | 1.3 ± 0.6 |
| EcRΔA/B | — | 1600 ± 265 | | 1719 ± 388 | | 1877 ± 311 | |
| EcRΔA/B | Usp | 1018 ± 185 | 0.6 ± 0.0 | 1361 ± 365 | 0.8 ± 0.8 | 1368 ± 197 | 0.8 ± 0.1 |
| EcR\mAR-DE | — | 541 ± 85 | | 357 ± 153 | | 7966 ± 1467 | |
| EcR\mAR-DE | Usp | 1479 ± 174 | 2.7 ± 0.1 | 2039 ± 415 | 6.0 ± 1.4 | 10762 ± 1577 | 1.4 ± 0.1 |
| mAR\EcR-CDEF | — | 98 ± 75 | | 75 ± 33 | | 33 ± 27 | |
| mAR\EcR-CDEF | Usp | 1082 ± 147 | 15 ± 10 | 1414 ± 184 | 20.0 ± 6.3 | 1431 ± 118 | 62.0 ± 50 |
| Receptors tested with the mouse androgen receptor response element | | | | | | | |
| — | — | 101 ± 25 | | 144 ± 24 | | 89 ± 70 | |
| — | Usp | 96 ± 91 | 0.9 ± 0.7 | 191 ± 23 | 1.33 ± 0.1 | 37 ± 20 | 0.7 ± 0.8 |
| mAR\EcR-DEF | — | 315 ± 51 | | 258 ± 38 | | | ND* |
| mAR\EcR-DEF | Usp | 183 ± 20 | 0.6 ± 0.0 | 229 ± 12 | 0.89 ± 0.1 | | ND |
| mAREcR-EF | — | 307 ± 52 | | 304 ± 52 | | | ND |
| mAR\EcR-EF | Usp | 2029 ± 122 | 6.7 ± 1.5 | 2054 ± 14 | 6.86 ± 1.1 | | ND |
| mAR\EcR-E | — | 304 ± 4 | | 281 ± 71 | | | ND |
| mAR\EcR-E | Usp | 2781 ± 214 | 9.2 ± 0.6 | 3751 ± 286 | 8.79 ± 3.2 | | ND |
| mAR-D\EcR-DEF | — | 322 ± 24 | | 246 ± 62 | | | ND |
| mAR-D\EcR-DEF | Usp | 2091 ± 247 | 6.5 ± 0.3 | 2022 ± 267 | 8.51 ± 1.0 | | ND |

ND *Not Detemined

The results of these experiments show that the high transcriptional activity present in EcR can be reduced such that a significant induction by Usp is detectable. The removal of the A/B domain from EcR resulted in EcRΔA/B, which retained constitutive activity and either was unaffected or repressed by the presence of Usp (1600±265 MU/mg and 1018±185 MU/mg, respectively); this profile is similar to that of EcR-B2. Adding back the A/B domain from mAR onto EcRΔA/B to form mAR\EcR-CDEF resulted in no detectable activity but inducibility by Usp (98±75 compared with 1082±147 MU/mg). Increasing the contribution from the N-terminal of mAR to include the C domain or D domain, resulted in mAR\EcR-DEF and mAR\EcR-EF and mAR-D\EcR-DEF, respectively, which have similar low constitutive activities of about 300 Mu/mg. Co-expression of Usp with the above chimeras decreases the activity of the first chimera and induces the other three to about 2000 MU/mg. The inability to induce mAR\EcR-DEF but the ability to induce mAR-D\EcR-DEF suggests that the D region from the mAR is an important region for the function of the DNA binding domain. This speculation is consistent with observations made previously with a truncated mAR. The inducibility of mAR\EcR-E (in which the F domain is absent) is similar to mAR\EcR-EF, (in which the F domain is present) suggesting that in this situation the F domain does not contribute to Usp function. The substitution of the N-terminal A/B and C domains of the EcR onto the mAR results in the chimera EcR\mAR-DE, which has a low basal activity and is Usp inducible.

6.0±1.4 to 9.2±0.6). These results suggest that Usp inducibility requires the presence of an A/B domain and that the A/B of mAR and of EcR are interchangeable for this function. These results also show that none of the EcRs, irrespective of the absence or presence of Usp, respond to Mur A. In contrast, EcR\mAR-DE is inducible by testosterone, from 541±367 MU/mg to 7966±1467 MU/mg, or a 17.6±8.47 fold increase. The basal and hormone induced levels obtained here with EcR\mAR-DE are similar to those reported with the complete mAR. Therefore, the mAR is more adaptable to using the A/B domain of the EcR, than the reverse situation. The induction of EcR/mAR-DE by testosterone in the presence of Usp appears to be slightly higher (from 7966±1467 MU/mg to 10,763±1577 MU/mg). This additional effect suggests that the induction by testosterone and Usp are elicited independently. The low basal activity of mAR/EcR-CDEF chimera was also selected because it contains the largest portion of the EcR relative to the other chimeras.

EXAMPLE 3

Method for Screening for Usp Inhibitory Compounds

Rationale: Canavanine/arginine permease (CAN1) is a membrane transporter for arginine and is the only means of entry of the toxic arginine analog, canavanine (Hoffmann, J.Biol.Chem., 260:11831, 1985). Yeast containing CAN1 fail to grow on appropriate concentrations of canavanine, while yeast deleted for can1 are resistant and viable; the sensitivity is semidominant since CAN1can1 cells are sensitive (Broach et al., Gene 8:121, 1979). This property has been exploited as a selectable marker for the isolation of mutant strains and cloned genes. The following experiment describes the use of CAN1 as an inducible reporter gene. In these experiments CAN1 is substituted for LacZ in a EcRE$_2$-reporter gene in a can1 yeast strain as an obligatory host, and canavanine is included in the growth medium. This results in the reduction of cell growth when Usp and mAR\EcR-CDEF are both present in the yeast strain as compared to when either is absent or alone.

FIGS. 2A and 2B a schematic representations of the transcriptionally regulated CAN1 system for monitoring rescue of cell growth and the reduction to practice of this system. The schematics show that can1 yeast cells transfected with YEpcUsp, YEpmAR\EcR-CDEF (designated "YEpCH8") and YEpEcRE-CAN1 accumulate the canavanine permease on their plasma membrane and canavanine intracellularly, leading to cell toxicity (FIG. 2A). However, in the presence of an inhibitor (I) to Usp transcription, CAN1 expression is inhibited (X) and cells growth occurs (FIG. 2B).

I. MATERIALS AND METHODS

A. Stock Solutions

10× Concentrated Yeast Nitrogen Base without Amino Acids (YNB)(Difco) was prepared by dissolving 67 g per liter, after which it was filter sterilized and stored at 4° C. Gold Concentrate (G-trp,-leu,-ura,-arg) contained the following components Adenine Sulfate 120 mg L-Histidine 120 mg L-methionine 120 mg L-tyrosine 180 mg L-isoleucine 180 mg L-lysine-HCl 180 mg L-phenylalanine 300 mg L-glutamic acid 600 mg L-aspartic acid 600 mg L-valine 900 mg L-threonine 1200 mg L-serine 2250 mg The components were dissolved in 1.1 liter H$_2$O. A few drops of 10 N NaOH were added to completely dissolve the amino acids, after which the solution was filter sterilized and stored at 4° C.

Cupric Sulfate (CuSO$_4$) (Sigma cat.#C-1297) 100 mM was prepared by dissolving 1.6 g per 100 ml dH$_2$O, filter sterilizing, and storing at RT protected from light.

Canavanine Stock (Can) (Sigma cat.#C-9758) was prepared by dissolving 100 mg per ml, filter sterilizing and storing at 4° C.

Arginine Stock (Arg) was prepared by dissolving 100 mg per ml, filter sterilizing and storing at 4° C.

B. Preparation of Gold Media:

Liquid Medium contained the following components:

12 g dextrose 60 ml 10× YNB 110 ml Gold Concentrate

600 µl Cupric Sulfate 430 ml dH$_2$O

The components were dissolved in a total volume of 600 ml, after which the solution was filter sterilized and stored at 4° C.

Agar Medium contained the following components:

12 g Dextrose 12 g Bacto Agar 430 ml dH$_2$O

The above ingredients were mixed and autoclaved for 20 minutes, after which the following reagents were added:

60 ml 10× YNB 110 ml Gold Concentrate

600 µl Cupric Sulfate in a total volume of 600 ml. After cooling in a 50° C. water bath for at least 20 minutes, 300 µl of the canavanine stock solution were added and mixed.

II. METHODS

The yeast strain CGY44:YEpmAR\EcR-CDEF/YEpcUSP/YEpEcRE$_2$-CAN1 was grown overnight from an individual clone in 5 ml liquid Gold media with shaking at 30° C. A 200 µl aliquot of the overnight culture was transferred to 50 ml liquid Gold medium and shaken at 30° C. overnight. The OD$_{600}$ of the culture was measured (approximately 1.0). A 6 ml aliquot of cells at an OD$_{600}$ of 1 was removed and mixed with 150 ml Gold Mix Medium Agar that had been precooled to 50° C. The mixture was poured into a large Sumilon screening dish.

After the agar solidified, the test samples were applied onto the plate. As a positive control, ¼ inch filter disks containing 50 and 100 µg arginine were used. The plate was incubated in a 30° C. incubator overnight and the plates were analyzed the next day. The arginine disks showed a zone of growth visible after 16 h of incubation (and more robust growth after 24 hours).

III. RESULTS

A. Assay Variability

To test for reproducibility within a given experiment and in multiple tries, the assay was performed independently five times within a three week period. Each experiment used newly grown yeast cells and newly prepared media. Filter disks containing samples listed in Table 4 were assayed on each plate. Only the disks containing arginine produced a zone of growth, with the 100 µg arginine giving the largest zone and 10 µg giving the smallest zone.

TABLE 4

| Sample | Amount | Compound |
| --- | --- | --- |
| 1 | 100 µg | Arginine |
| 2 | 10 µg | Penicillin |
| 3 | 30 µg | Vancomycin |
| 4 | 25 µg | Rafampin |
| 5 | 30 µg | Kanamycin |
| 6 | 50 µg | Arginine |
| 7 | 10 µg | Gentamycin |
| 8 | 30 µg | Tetracyclin |
| 9 | 2 µg | Linomycin |
| 10 | 100 µg | Nitrofurontoin |
| 11 | 20 µg | Arginine |
| 12 | 30 µg | Amikacin |
| 13 | 30 µg | Novobiocin |
| 14 | 15 µg | Erythromycin |
| 15 | 5 µg | Trimetoprim |
| 16 | 10 µg | Arginine |

B. Limit of Detection

An antagonist for ultraspiracle is not known. As an alternative, arginine (which specifically completes with canavanine for transport by the arginine permease) was used to determine the minimum concentration of a compound that could rescue the yeast. Various concentrations (1, 2, 5, 10, 20, 30, 40, 50, 60, 70, 80, 90, 100, 200, 400 and 800 µg) of arginine were placed on filter disks. A zone of growth was visible around the disk containing 10 μg and greater. Therefore, the sensitivity of the screen is 10 μg of arginine. However, an inhibitor specific for ultraspiracle may have a much lower limit.

Table 5 quantifies the diameter of decreased (A) or increased (B) cell growth around filter disks spotted with canavanine and arginine, respectively, and grown in the absence (A) or presence (B) of canavanine.

TABLE 5

A

Canavanine on Filter   can 1 yeast containing EcRE$_2$-CAN1, mAR/EcR-CDEF and

| Disk (μg/ml) | Usp | Vector |
|---|---|---|
| | Diameter of Zone of Diminished Growth (mm) | |
| 2 | 13 | ND* |
| 10 | 17 | ND |
| 50 | 27 | ND |
| 100 | 31 | ND |

B

| Arginine on | Canavanine in Medium (μg/ml) | | | |
|---|---|---|---|---|
| Filter Disk (μg/ml) | 2 | 10 | 50 | 100 |
| | Diameter of Zone of Cell Growth (mm) | | | |
| 2 | 15 | 8 | ND | ND |
| 10 | 23 | 15 | 10 | 8 |
| 50 | 31 | 24 | 18 | 16 |
| 100 | 34 | 28 | 22 | 20 |

*ND not detectable

Yeast cells containing mAR\EcR-CDEF, YEpEcRE$_2$-CAN1 and Usp respond to the presence of canavanine (spotted on a filter disk) by producing larger zones of growth inhibition, as compared to comparable cells not containing Usp which have no detectable inhibitor zones (Panel A Usp column vs. Vector column). These results show that at 50 μg canavanine on the disk a zone size of 27 mm was reached. This is near maximum and probably diffusion limited, because by doubling the canavanine to 100 μg the zone increases only marginally to 31 mm. The additional control of yeast cells containing YEpecRE$_2$-CAN1 and Usp also showed no zones. The reverse assay produced corresponding results.

When cells expressing mAR\EcR-CDEF, Usp and CAN1 are grown on canavanine containing media the presence of arginine on the disk rescues cells (Panel B). For rescue, the concentration of arginine and canavanine are directly related; as the concentration of canavanine increases more arginine is required to produce a zone of rescue. With 50 μg/ml canavanine in the agar medium, 10 μg arginine on a disk produced a small zone of 10 mm while 100 μg arginine gave larger zones of 22 mm. The zone toxicity to canavanine or rescue by arginine are most prominent after 16 hr of growth and subsequently they are diffused out by background growth. Increasing the amount of canavanine in the agar up to 1 mg did not prevent the yeast strain with the complete system from growing. In contrast, growth of wildtype cells is suppressed completely by 2 μg/ml canavanine. This difference may arise from the presence in the engineered strain of fewer arginine permeases in the wildtype strain; the reporter plasmid is induced to a very low level, as shown in Table 3 above.

Second, a minimal number of arginine permeases are required to kill the cell; when the engineered strain divides, differential segregation of the reporter plasmid may result in daughter cells with too low a level of permeases to confer canavanine sensitivity. These reasons are consistent with the reported property that sensitivity to canavanine is semidominant since CAN1/can1 diploid cells show intermediate sensitivity.

C. Compatibility of Fermentation Media

The effects of fermented and fresh fungal media on the assay were determined by placing filter disk containing 20 μl of each broth or media blank on the test plate. As a control, blank media containing 100 μg arginine was also tested. As the results in Table 6 show, the nine media (A1, AA, B, F-1, B, L-1, FM7, FM2, and FM3 refer to media codes in present use at Pearl River) tested had no effect on the screen whether they were fermented with a culture or not.

TABLE 6

| Culture # | Media | Zone of Growth |
|---|---|---|
| Marine-F92S-93 | A1 | No |
| Marine-F92S-93 | AA | No |
| Marine-F92S-94 | B | No |
| Blank | A1 | No |
| Blank | AA | No |
| Blank | B | No |
| Arginine | A1 | Yes |
| Arginine | AA | Yes |
| Arginine | B | Yes |
| Actino-LC-41C-2 | F-1 | No |
| Actino-LC-41C-3 | B | No |
| Actino-LC-41C-4 | L-1 | No |
| Blank | F-1 | No |
| Blank | B | No |
| Blank | L-1 | No |
| Arginine | F-1 | Yes |
| Arginine | B | Yes |
| Arginine | L1 | Yes |
| Fungus-PP5965 | FM7 | No |
| Fungus-PP5966 | FM2 | No |
| Fungus-PP5967 | FM3 | No |
| Blank | FM7 | No |
| Blank | FM2 | No |
| Blank | FM3 | No |
| Arginine | FM7 | Yes |
| Arginine | FM2 | Yes |
| Arginine | FM3 | Yes |

The above-described system has been implemented in a high-throughput screening format for synthetic compounds and natural products; the percentage of rescue is of 0.01%. To eliminate non-specific leads, putative leads are tested on wildtype CAN1 strain grown in 2 μg/ml canavanine. If rescue occurs, the lead is discarded; if it does not, it is retained and evaluated further. Non-specific leads have included the antifungal compound nystatin, compounds that block the arginine permease, and tryptophane, which caused the loss of the YEpmAR\EcR-CDEF plasmid which has TRP1 as the selectable marker. This observation may indicate that the co-expression of the EcR and Usp is essential for cell death.

For additional secondary screens to determine the specificity of putative leads, strains containing either YEpEcR-B1, YEpEcR-A, YEpEcR-B2, or the YEpEcR\mAR-DE, and YEpEcRE$_2$-CAN1, with or without YEpcUsp, can be used. Their sensitivity to canavanine is shown in Table 7. The EcR isoforms all produce a zone of no growth surrounding a filter disk containing 100 μg of canavanine (34, 17, and 17 mm, respectively) as compared to their absence (12 mm). Usp, which, by itself, has no effect (12 mm zone), potentiated all three EcR isoforms (producing zones of 42, 34, and 25 mm, respectively). Yeast cells expressing mAR\EcR-CDEF and Usp gave a zone of growth arrest of 27 nM. The cells containing EcR\mAR-DE in the absence and presence of Usp were insensitive; however, in the presence of testosterone they produced zone of 36 nM. Cells containing EcRΔA/B were insensitive, and co-expression of Usp had no effect. These results are consistent with the β-galactosidase results (Tables 2 and 3), except that, here, Usp clearly potentiates the EcR-B2 isoform. In addition, these results indicate that these strains can be used as secondary screens to confirm leads. Furthermore, they suggest that the canavanine assay as compared to the β-galactosidase assay may be less quantitative but more sensitive, i.e., EcR-B2 shows comparable sensitivity to canavanine as EcR-A (17 mm zone), while it induces less β-galactosidase expression (480±150 versus 6694±3187, respectively; Table 2); and EcR-B2 in the presence as compared to the absence of Usp shows a significantly increased sensitivity to canavanine (25 mm versus 17 mm zone, respectively) but the same situation with the β-galactosidase assay is less clear (0.9±1.5 induction due to the presence of Usp, Table 2).

TABLE 7

A can1 Yeast Containing EcRE$_2$-CAN1 and

| EcR Form | Vector | | Usp | |
|---|---|---|---|---|
| | Diameter of Zone of Diminished Growth (mm) | | | |
| — | 12[1] | | 12 | |
| EcR-B1 | 34 | | 42 | |
| EcR-A | 17 | | 34 | |
| EcR-B2 | 17 | | 25 | |
| EcR\mAR-DE[2] | 12[2] | 30[4] | 12[3] | 41[4] |

[1]12 mm represents; [2]untreated and [3]testosterone treated cells
Results are the averages two independent clones, and are from two or more independent experiments.

B. CANAVANINE SENSITIVITY-zones of no growth can1 Yeast Containing EcRE$_2$-CAN1 and

| EcR Form | Vector | Usp | RXRα |
|---|---|---|---|
| | Diameter of Zone of Diminished Growth (mm) | | |
| — | 15[1] | 13 | 12 |
| EcRΔA/B | 22 | 20 | 29 |
| mAR\EcR-CDEF | 15 | 26 | 15 |

C. β-Galactosidase Activity-LacZ induction

Nuclear Receptor

| EcR Form | Vector | Usp | RXRα |
|---|---|---|---|
| | β-Galactosidase Activity (MU/mg) | | |
| — | 93 ± 53 | 107 ± 53 | 56 |
| EcRΔA/B | 2085 ± 509 | 1350 ± 291 | 4320 ± 1230 |
| mAR\EcR-CDEF | 83 ± 25 | 726 ± 246 | 128 ± 94 |

E. RXRα and Usp May Not be Interchangeable in Yeast

Since RXRα can substitute for Usp in binding and transactivation in yeast, experiments were performed to test whether substitution of RXRα for Usp would be useful to confirm putative leads. This was done first by using the canavanine assay (Table 7, Panel B) and confirmed using the β-galactosidase assay (Table 7, Panel C). The results show that RXRα transactivates the N-terminal truncated EcR (EcRΔA/B) but not the chimeric receptor mAR/EcR-CDEF. This is the reverse of Usp, which does not activate EcRΔA/B but does activate mAR/EcR-CDEF. Yeast containing YEpEcRE$_2$-CAN1 in the absence or presence of either Usp or RXRα do not show sensitivity to canavanine, i.e. exhibited no significant zone surrounding a filter disk spotted with 100 μg canavanine (15, 13, and 12 mm, respectively). Yeast containing YEpEcRE$_2$-CAN1 and EcRΔA/B show a zone of no growth (22 mm) which is not affected by the additional presence of Usp (20 mm) but which is enlarged by the presence of RXRα (29 mm). In contrast, yeast containing YEpEcRE$_2$-CAN1 and mAR/EcR-CDEF show no sensitivity to canavanine and the additional presence of RXRα has no effect (15 mm zone), but the additional presence of Usp produces a larger zone (26 mm).

For accumulation of β-galactosidase the same pattern is seen. Cytosolic extracts prepared from yeast containing YEpEcRE$_2$-LacZ alone or with either Usp or RXRα do not accumulate a significant level of β-galactosidase activity. The additional presence of EcRΔA/B results in a basal activation of the reporter gene (2085±509 MU/mg), which is unaffected or even repressed by the presence of Usp (1350±291 MU/mg) but is increased by the presence of RXRα (4320±1230 MU/mg). The reverse is true with mAR/EcR-CDEF, which, alone or in the presence of RXRα, has no effect (83±25 MU/mg and 238±94 MU/mg, respectively), but in the presence of Usp increases (726±246 MU/mg).

In summary, RXRα and Usp are not interchangeable, but strains containing them can be used to evaluate the specificity of lead compounds identified by the assay.

Alternatively, since RXRα has been reported to transactivate the vitamin D receptor (VDR) in yeast, we wanted to determine if Usp could substitute for RXRα in activating the strain and determined the canavanine sensitivity. For the preliminary determination we used the plasmid with LacZ as the reporter gene. A duplicate copy of a 25 base pair sequence derived from hOC, which is a reported HRE for VDR, was inserted into the reporter plasmid, and the resulting reporter plasmid YEpVDRRE$_2$-LacZ was tested in the appropriate yeast strains. The results provided in Table 8 show that cytosolic extracts of yeast strains containing both RXRα and hVDR have more β-galactosidase activity than strains containing either receptor alone, 1320±50 MU/mg, 520±360 MU/mg, 96±9 MU/mg, respectively, but those containing Usp and hVDR have about the same level that cells containing just Usp do, 473±110 MU/mg and 520±0 MU/mg, respectively. Interestingly, cells with the reporter alone have 175±59 MU/mg of β-galactosidase activity, suggesting that Usp alone has transcriptional activity which is detectable with this reporter plasmid.

TABLE 6

| Nuclear Receptors | | | β-Galactosidase Activity (Mu/mg) | |
|---|---|---|---|---|
| hVDR | RXRγ | Usp | No Treatment | 1,25(OH)$_2$D$_3$ |
| — | — | — | 175 ± 59 | 169 ± 86 |
| hVDR | — | — | 96 ± 9 | 64 ± 11 |
| — | RXRα | — | 520 ± 360 | 334 ± 192 |
| — | — | Usp | 473 ± 110 | 339 ± 65 |
| hVDR | RXRα | — | 1320 ± 50 | 1150 ± 456 |
| hVDR | — | Usp | 520 ± 0 | 600 ± 0 |

Therefore, this is a second observation using yeast in which RXRα and Usp are not interchangeable as heterodimeric partners for a nuclear receptor. In considering what EcRΔA/B and VDR may have in common, a striking similarity is that EcRΔA/B has no A/B domain, and VDR has a very small one (only 21 amino acids). This observation is consistent with the results obtained using EcR-B2 and Usp.

F. Screening a Set of Natural Products

A set of natural products (6,500 samples) with known and diverse activities was assayed by transferring 10 to 20 μg of each compound onto the agar test plate using a 96-well replica plate. Three compounds produced a zone of killing surrounded by a zone of growth, and have been identified as potential lead compounds.

G. Screening of DIVPIK Compounds

The 6592 samples in the DIVPIK collection (an assortment of chemical compounds representing various chemical classes) were screened at an amount of 5–10 µg. No obvious positives were detected. However, 5 compounds produced a zone of killing surrounded by a zone of growth similar to the four compounds. These preliminary hits were tested further in the secondary screen where the compounds again produced the same phenotype. Since these hits were inhibiting the arginine permease and not ultraspiracle, they were not scored as positives. Therefore, no compound in the DIVPIK collection was found to specifically inhibit ultraspiracle.

H. Screening of a Synthetic Library

Over 38,000 samples in a synthetic library have been screened using the methods of the present invention. Two positive samples were identified.

All patents, patent applications, articles, publications, and test methods mentioned above are hereby incorporated by reference in their entirety.

Many variations of the present invention will suggest themselves to those skilled in the art in light of the above detailed description. Such obvious variations are within the full intended scope of the invention.

We claim:

1. A method for identifying compounds that inhibit the transcription promotion function of Drosophila ultraspiracle protein (Usp), said method comprising:

(i) providing a transformed yeast cell comprising:
  (a) a Usp binding partner wherein the Usp binding partner is a member of a nuclear receptor family;
  (b) Usp or derivatives thereof containing an apparent domain structure typical of the nuclear steroid receptor family, including an A/B (transactivation) domain, a C (DNA binding/dimerization/transactivation) domain, a D (nuclear localization) domain, and an E (dimerization) domain capable of forming a functional Usp—Usp binding partner complex with said Usp binding partner; and
  (c) a reporter gene, wherein expression of said reporter gene is transcriptionally activated by said functional Usp—Usp binding partner complex and whose expression in yeast is readily detectable in said transformed yeast cell;

(ii) incubating said transformed yeast cell in the presence of a test compound to form a test culture, and in the absence of a test compound to form a control culture; and (iii) monitoring expression of said reporter gene in said test and control cultures.

2. A method as defined in claim 1, further comprising (iv) identifying as a compound that inhibits the function of Usp any compound that reduces the expression of said reporter gene in said test culture relative to said control culture.

3. A method for identifying compounds that inhibit the transcription promotion function of Drosophila ultraspiracle protein (Usp), said method comprising:

(i) providing a transformed yeast cell comprising:
  (a) a Usp binding partner wherein the Usp binding partner is a member of a nuclear receptor family;
  (b) Usp or derivatives thereof containing an apparent domain structure typical of the nuclear steroid receptor family, including an A/B (transactivation) domain, a C (DNA binding/dimerization/transactivation) domain, a D (nuclear localization) domain, and an E (dimerization) domain capable of forming a functional Usp—Usp binding partner complex with said Usp binding partner; and
  (c) a reporter gene, wherein expression of said reporter gene is transcriptionally activated by said functional Usp—Usp binding partner complex and whose expression in yeast is readily detectable in said transformed yeast cell;

(ii) incubating said transformed yeast cell in the presence of a test compound to form a test culture, and in the absence of a test compound to form a control culture;

(iii) monitoring expression of said reporter gene in said test and control cultures to detect a compound that reduces the expression of said reporter gene in said test culture relative to said control culture.

4. A method as defined in claim 1, wherein said yeast is selected from the group consisting of S. cerevisiae and S. pombe.

5. A method as defined in claim 1, wherein said Usp binding partner comprises mAR\EcR-CDEF.

6. A method as defined in claim 5, wherein said reporter gene comprises DNA encoding CAN1 derived from S. cerevisiae operably linked to an ecdysone-responsive transcriptional activation sequence.

7. A method as defined in claim 1, wherein said Usp binding partner is selected from the group consisting of vitamin D receptor, retinoic acid receptor, ecdysone receptor, thyroid hormone receptor, peroxisome proliferator-activated receptor, and DHR38.

8. A method as defined in claim 7, wherein said reporter gene comprises DNA encoding CAN1 derived from S. cerevisiae operably linked to a DNA sequence selected from the group consisting of an ecdysone response element, androgen response element, Vitamin D response element, retinoic acid response element, and peroxisome proliferator response element.

9. A method as defined in claim 6, wherein said monitoring is achieved by the steps of:
  (i) exposing said test and control cultures to canavanine under conditions in which said control cultures exhibit significant growth; and
  (ii) detecting test cultures in which growth is inhibited relative to growth of said control cultures.

* * * * *

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
       (A) LENGTH: 37 base pairs
       (B) TYPE: nucleic acid
       (C) STRANDEDNESS: single
       (D) TOPOLOGY: linear (xi) SEQUENCE DESCRIPTION: SEQ ID NO:1:

ACTTCACGGC CGATGGACAA CTGCGACCAG GACGCCA                                37

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:2:

CACCTGGGCA AAGTGCGGCA TCAT                                             24

(2) INFORMATION FOR SEQ ID NO:3:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:3:

CAAACAGCTC TTCCAGATGG TCGA                                             24

(2) INFORMATION FOR SEQ ID NO:4:

(i) SEQUENCE CHARACTERISTICS:
       (A) LENGTH: 39 base pairs
       (B) TYPE: nucleic acid
       (C) STRANDEDNESS: single
       (D) TOPOLOGY: linear (xi) SEQUENCE DESCRIPTION: SEQ ID NO:4:

ACTACTCAAA CAGTGCTACT CCAGTTTCAT CGCCAGGCC                             39

```
(2) INFORMATION FOR SEQ ID NO:5:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO:5:

TTAAGACTAA GAGGTGGTAT GAAGCGGCGC TGGTCGAACA ACGGCGGCTT CATGCCTACC        60

GGAGGCGGCC GTCCGGACGG CCGGGTAC                                          88

(2) INFORMATION FOR SEQ ID NO:6:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO:6:

CCGGCCGTCC GGACGGCCGC CTCCGGTAGG CATGAAGCCG CCGTTGTTCG ACCAGCGCCG        60

CTTCATACCA CCTCTTAGTC                                                   80

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:7:

AGGAGATCTG GGACGTTCAT GCCAT                                             25

(2) INFORMATION FOR SEQ ID NO:8:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:8:

TAAACGCGTT CCGGACTATG CAGTCGTCGA GTGCTCCGAC TTAAC                       45

(2) INFORMATION FOR SEQ ID NO:9:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:9:

CTTGTCTTAA GACTAAGAGG TGGCATGGAT ACTTGTGGAT TAGT                        44

(2) INFORMATION FOR SEQ ID NO:10:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:10:
```

```
CTTGTCTTAA GACTAAGAGG TGGCATGTTG ACGACGAGTG GACA                          44
```

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:11:

```
GCACTCCTGA CACTTTCGCC TCAT                                                24
```

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:12:

```
ATGTGTCAGA GGTTTTCACC G                                                   21
```

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:13:

```
TCATCACACG TGGTTGGCCA AGACAAG                                             27
```

(2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:14:

```
TCATCACACC ACGTGGAGCT GTGCCTGGTT TGCGGCGAC                                39
```

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:15:

```
CTCTCTTCAA CCCACCAAAG GCCA                                                24
```

(2) INFORMATION FOR SEQ ID NO:16:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:16:

```
CATCATGAGC TCTCGTAAGC TGAAGAAACT TGGAAATCT                                39
```

(2) INFORMATION FOR SEQ ID NO:17:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:17:

CATCTTCTCC GGATCACTGT GTGTGGAAAT AGATGGGCT                        39

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:18:

CATGATCACA CAGTGCAGAT GTATGAGCAG CCATCT                          36

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:19:

GATCTAGCGC GCCTATGCAG TCGTCGAGTG CTCCGA                          36

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:20:

GATCTAGCGC GCCTAAAGGT GCGACTGGAC CGATGG                          36

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:21:

TCATCACACC ACGTGATGGA GGTGCAGTTA GGGCTGGGA                       39

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:22:

TCATCACACG TGGTGGGTCT TCTGGGGTGG AAAGTAATA                       39

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:23:

TCGAGTAGGT CACGTAAATG TCCA                                   24

(2) INFORMATION FOR SEQ ID NO:24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:24:

TCGAGCCTGG ACATTTACGT GACCTAC                              27

(2) INFORMATION FOR SEQ ID NO:25:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:25:

TCGAGGACAA GTGCATTGAA CCTGTCTCCC GGGC                       34

(2) INFORMATION FOR SEQ ID NO:26:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:26:

TCGAGCCCGG GAGACAAGGG TTCAATGCAC TTGTC                    35

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:27:

TCGAGCTTAC CGGGTGAACG GGGGCATTAC                           30

(2) INFORMATION FOR SEQ ID NO:28:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:28:

TCGAGTAATG CCCCCGTTCA CCCGGAAGC                            29

-continued (2) INFORMATION FOR SEQ ID NO:29:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:29:

GTGCTCGGAT CCATGACAAA TTCAAAAGAA GACG    34

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:30:

TGGTGGGAGC TCCTATGCTA CAACATTCC    29